United States Patent [19]

Amuti et al.

[11] Patent Number: 4,645,527

[45] Date of Patent: Feb. 24, 1987

[54] HERBICIDAL ANTIDOTES

[75] Inventors: Kofi S. Amuti; Philip B. Sweetser, both of Wilmington, Del.

[73] Assignee: E. I. Du Pont de Nemours and Company, Wilmington, Del.

[21] Appl. No.: 681,963

[22] Filed: Dec. 14, 1984

[51] Int. Cl.[4] .................... A01N 47/28; A01N 47/36
[52] U.S. Cl. ........................... 71/90; 71/103; 71/93
[58] Field of Search ............... 71/90, 103, 93

[56] References Cited

U.S. PATENT DOCUMENTS

| | | | |
|---|---|---|---|
| 4,021,229 | 5/1977 | Arneklev et al. | 71/103 |
| 4,168,152 | 9/1979 | Gaughan et al. | 71/103 |
| 4,434,000 | 2/1984 | Mahoney et al. | 71/103 |
| 4,481,029 | 11/1984 | Levitt | 71/93 |

FOREIGN PATENT DOCUMENTS

| | | | |
|---|---|---|---|
| 42-9276 | 5/1967 | Japan | 71/103 |
| 6910209 | 1/1971 | Netherlands | 71/103 |

OTHER PUBLICATIONS

"Weed Control Handbook: Principles", (Handbook), Roberts, ed., (Blackwell Scientific, 1982), pp. 135–142.
Ray, "Plant Physiology", vol. 75, pp. 827–831, (1984).

*Primary Examiner*—Glennon H. Hollrah
*Assistant Examiner*—Robert Lelkes

[57] ABSTRACT

Compositions comprising a non-phytotoxic antidotal compound and an antidotable herbicide and the use of the compositions to protect crop plants from injury due to the herbicide.

10 Claims, No Drawings

HERBICIDAL ANTIDOTES

BACKGROUND OF THE INVENTION

1. Field of the Invention

This invention relates to sulfonylurea compositions of a non-phytotoxic antidotal sulfonylurea compound and a sulfonylurea hericidal and methods for using the compositions to protect cereal crops from injury from the herbicide.

2. Description of the Prior Art

It is difficult to find herbicidal compounds which exhibit sufficient selectivity to control weeds but not damage useful crop plants. In many cases, antidotes have been found which, when applied in combination with a particular herbicide, act to protect the useful crop plant from damage caused by the herbicide but which do not adversely affect the action of the herbicide on weeds.

U.S. Pat. Nos. 3,564,768, and 3,782,759 disclose that 1,8-naphthalic anhydride can be applied to corn seeds to protect corn plants from damage caused by N,N-dialkylthiocarbamate ester pre-emergent herbicides as well as other herbicides. According to U.S. Pat. No. 3,749,566, 1,8-naphthalic anhydride is also useful for protecting rice from N,N-dialkylthiocarbamate ester herbicide damage.

U.S. Pat. No. 4,070,389, discloses that α-(cyanomethoxyimino)benzacetonitrile products crops from damage caused by triazine, phenylurea, carbamate, benzoic acid derivative and halogenated phenoxyacetic acid herbicides.

U.S. Pat. No. 4,021,224, U.S. Pat. No. 4,124,376, and U.S. Pat. No. 4,137,070, disclose the use of N,N-diallyl-2,2-dichloroacetamide as an antidote for thiocarbamate and haloacetanilide herbicides.

U.S. Pat. No. 4,343,649 discloses that cereal crops can be protected from injury due to a herbicidal compound selected from 2-chloro-N-[(4-methoxy-6-methyl-1,3,5-triazin-2-yl)aminocarbonyl]benzenesulfonamide, 2,5-dichloro-N-[(4,6-dimethoxypyrimidin-2-yl)-aminocarbonyl]benzenesulfonamide and 2-carbomethoxy-N-[(4,6-dimethylpyrimidin-2-yl)aminocarbonyl]benzenesulfonamide by combining application of said herbicide to the locus of said crop plant with application of a non-phytotoxic, antidotally-effective amount of an antidotal compound selected from 1,8-naphthalic anhydride, N,N-diallyl-2,2-dichloroacetamide, and α-(cyanomethoxyimino)benzacetonitrile to the crop seed, to the crop plant or to the locus of the crop plant.

U.S. Pat. Nos. 4,021,229 and 4,266,078 disclose various sulfonamide derivatives as antidotes for thiocarbamates, acetanilide or haloacetanilide herbicides.

None of the above patents discloses or teaches the use of sulfonylurea antidotes with sulfonylurea herbicides of this invention.

SUMMARY OF THE INVENTION

The composition of the invention protects agricultural crops, especially cereal crops, from injury while a sulfonylurea herbicide controls undesired vegetation. The composition of the invention consists essentially of an antidotally-effective amount of a compound of Formula I, or its agriculturally suitable salt and a sulfonylurea herbicide.

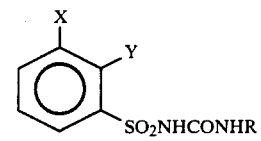

wherein
X is H, F, Cl or Br;
Y is Cl or $SO_2NR^1R^2$;
R is H, $C_1-C_6$ alkyl, $C_5-C_6$ cycloalkyl, benzyl or $C_2-C_4$ alkyl substituted with $C_1-C_2$ alkoxy or $C_1-C_2$ alkylthio;
$R^1$ and $R^2$ are independently $C_1-C_2$ alkyl; provided that when Y is $SO_2NR^1R^2$, R is other than H or $CH_3$.

For reasons of greater antidotal efficacy and/or ease of synthesis the compound of formula I wherein
X is H or Cl;
Y is Cl or $SO_2N(CH_3)_2$; and
R is H, $C_1-C_6$ alkyl or $C_5-C_6$ cycloalkyl is preferred.

The following compounds of Formula I are most preferred for reasons of greater antidotal efficacy and/or ease of synthesis: N'-butylaminocarbonyl-3-chloro-N,N-dimethyl-1,2-benzenedisulfonamide; N-(cyclopentylaminocarbonyl)-2,3-dichlorobenzenesulfonamide; N-(aminocarbonyl)-2,3-dichlorobenzenesulfonamide; or N-(aminocarbonyl)-2-chlorobenzenesulfonamide.

With respect to the sulfonylurea herbicides of this invention, the preferred compositions consist essentially of a non-phytotoxic, antidotally-effective amount of a compound of Formula I and a herbicidally-effective amount of a suitable, antidotable sulfonylurea herbicide of Formulae II–VIII.

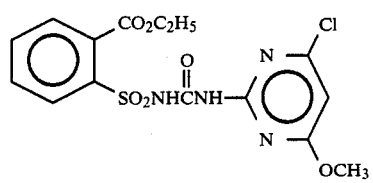

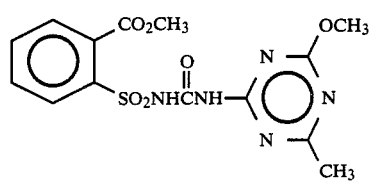

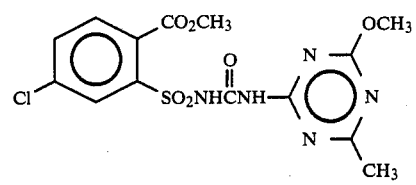

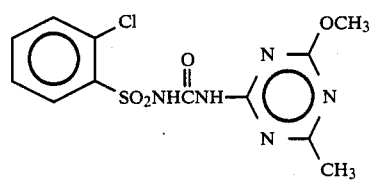

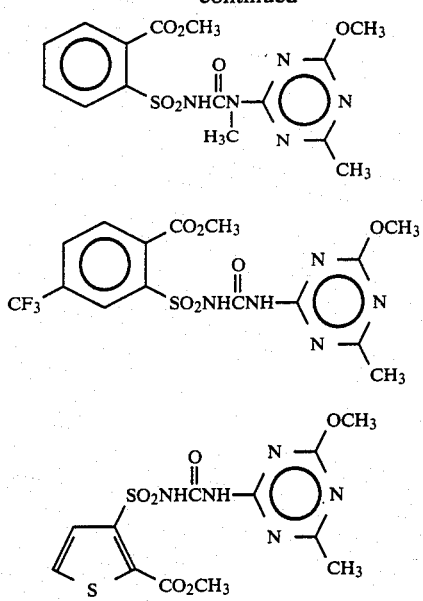

The most preferred herbicide/antidote compositions for reasons of greater efficacy, selectivity and/or herbicidal activity are: N-[(4-methoxy-6-methyl-1,3,5-triazin-2-yl)aminocarbonyl]-2-chlorobenzenesulfonamide (Compound V) with N'-butylaminocarbonyl-3-chloro-N,N-dimethyl-1,2-benzenedisulfonamide, 3-[[(4-methoxy-6-methyl-1,3,5-triazin-2-yl)aminocarbonyl]aminosulfonyl]-2-thiophenecarboxylic acid, methyl ester (Compound VIII) with N-(aminocarbonyl)-2,3-dichlorobenzenesulfonamide, and 3-[[(4-methoxy-6-methyl-1,3,5-triazin-2-yl)aminocarbonyl]aminosulfonyl]-2-thiophenecarboxylic acid, methyl ester (Compound VIII) with N-(aminocarbonyl)-2-chlorobenzenesulfonamide.

A method of using the compositions of the invention involves applying an antidotally-effective amount of a compound of Formula I in conjunction with the early post-emergence application to the locus of the crop plant of a suitable, antidotable sulfonylurea herbicide.

However, the preferred method of use involves applying an antidotally-effective amount of a compound of Formula I to the cereal crop seed to be protected, followed by the early postemergence application to the locus of the crop plant of a suitable antidotable sulonylurea herbicide. The antidotable sulfonylurea herbicides are preferably compounds II–VIII.

Another preferred method of use for reasons of greater antidotal efficacy, increased crop selectivity and/or greater herbicidal activity involves the application of a compound of Formula I to the cereal crop seed in conjunction with the early postemergence application of a sulfonylurea herbicide selected from the compounds of Formulae II–VIII.

The more preferred method of use involves the application of a compound of Formula I to the cereal crop seeds in conjunction with the postemergence application of 3-[[(4-methoxy-6-methyl-1,3,5-triazin-2-yl)aminocarbonyl]-aminosulfonyl]-2-thiophenecarboxylic acid, methyl ester (Compound VIII).

The most preferred method of use for reasons of greatest crop selectivity and herbicidal efficacy is the application of N-(aminocarbonyl)-2,3-dichlorobenzenesulfonamide to the cereal crop seeds in conjunction with the postemergence application of 3-[[(4-methoxy-6-methyl-1,3,5-triazin-2-yl)aminocarbonyl]aminosulfonyl]-2-thiophenecarboxylic acid, methyl ester (Compound VIII). This particular composition is most effective in controlling broadleaf weeds in corn.

More specifically preferred for reasons of greater efficacy, selectivity and/or herbicidal activity is the method of using the composition comprising N-[(4-methoxy-6-methyl-1,3,5-triazin-2-yl)aminocarbonyl]-2-chlorobenzenesulfonamide (Compound V) with N'-butylaminocarbonyl-3-chloro-N,N-dimethyl-1,2-benzenedisulfonamide to control weeds in sorghum.

Also preferred for reasons of greater efficacy, selectivity and/or herbicidal activity is the method of using 3-[[(4-methoxy-6-methyl-1,3,5-triazin-2-yl)-aminocarbonyl]aminosulfonyl]-2-thiophenecarboxylic acid, methyl ester (Compound VIII) with N-(aminocarbonyl)-2,3-dichlorobenzenesulfonamide or 3-[[(4-methoxy-6-methyl-1,3,5-triazin-2-yl)aminocarbonyl]aminosulfonyl]-2-thiophenecarboxylic acid, methyl ester (Compound VIII) with N-(aminocarbonyl)-2-chlorobenzenesulfonamide to control weeds in corn.

DETAILED DESCRIPTION OF THE INVENTION

Synthesis

Compounds of Formula I are prepared as shown in Equation I by the reaction of an appropriately substituted benzenesulfonyl isocyanate IX with an amine of Formula X.

Equation 1

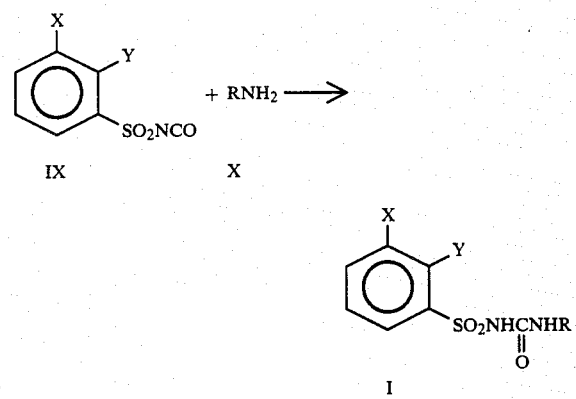

wherein
R, X and Y are as previously defined.

The reaction is generally exothermic and is best carried out in inert, aprotic solvents such as methylene chloride, tetrahydrofuran or acetonitrile, at ambient temperature and pressure. In some cases, the desired product is insoluble in the reaction medium and crystallizes in pure form. Products soluble in the reaction medium may be isolated by evaporation of the solvent and trituration or recrystallization with an appropriate solvent.

Alternatively, the compounds of Formula I, wherein R is other than H, can be prepared as shown in Equation 2 by the reaction of an appropriately substituted benzenesulfonamide XI with an isocyanate of Formula XII.

Equation 2

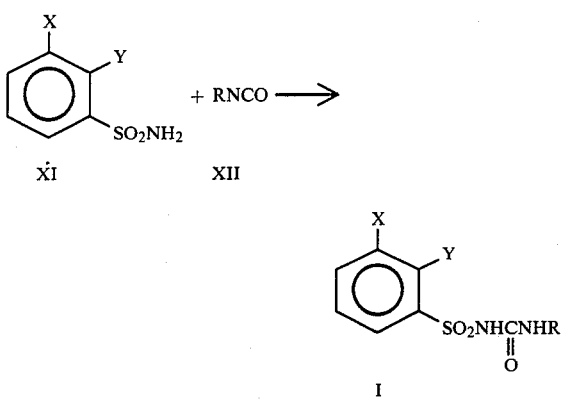

wherein

R, X and Y are as previously defined except R is other than H.

This reaction can be carried out by mixing stoichiometric amounts of the sulfonamide, isocyanate and a base such as potassium carbonate in a polar solvent such as acetone or methyl ethyl ketone at ambient to reflux temperature. The reaction mixture is poured into water and neutralized with hydrochloric or similar acid to precipitate the product.

Suitable sulfonyl isocyanates and sulfonamides, wherein Y is $SO_2NR^1R^2$, may be prepared as described in U.S. Pat. No. 4,310,346 which is herein incorporated by reference. Suitable sulfonyl isocyanates and sulfonamides, wherein Y is Cl, may be prepared as described in U.S. Pat. No. 4,169,719 which is herein incorporated by reference.

Agriculturally suitable salts of the antidotes of Formula I can be prepared by methods known in the art. Suitable salts include alkali metal or alkaline earth metal salts, e.g., potassium, sodium or calcium salts; quaternary amine salts; and acid addition salts, e.g., p-toluenesulfonic acid or trichloroacetic acid addition salts.

The following examples further illustrate the preparation of compounds of Formula I.

EXAMPLE 1

2-Chloro-N,N-dimethylbenzenesulfonamide

A stirred solution of 63.3 g of 2-chlorobenzensulfonyl chloride in 500 mL of tetrahydrofuran was cooled to 0°–5° C. and treated with 46 mL of dimethylamine, added dropwise at a rate that maintained the temperature below 10° C. The resulting mixture was allowed to warm gradually to room temperature. The precipitate was removed by filtration, and was washed well with tetrahydrofuran. The combined filtrates were evaporated in vacuo and the resulting oil was dissolved in 400 mL of methylene chloride, washed with two 200-mL portions of water, and dried over $MgSO_4$. Evaporation of the solvent in vacuo afforded an oil, which solidified upon standing. Trituration with hexanes afforded 58.6 g of 2-chloro-N,N-dimethylbenzenesulfonamide as a white solid, m.p. 49°–51° C.; NMR ($CDCl_3$): $\delta 2.9$ (s, 6H), 7.3–7.7 and 7.9–8.2 (m, 4H); IR(KBr): 1340 and 1170 cm$^{-1}$.

EXAMPLE 2

3-Chloro-2-(N,N-dimethylsulfamoyl)benzenesulfonyl-chloride

To a stirred mixture of 29 g of 2-chloro-N,N-dimethylbenzenesulfonamide and 150 mL ether at $-5°$ C. to 0° C. was added dropwise under nitrogen 94 mL of a 1.55M solution of n-butyllithium in hexanes. When the addition was complete, the reaction mixture was allowed to warm to room temperature and was stirred for 2 hours. The reaction mixture was then recooled to $-30°$ C. to $-20°$ C., and treated with a solution of 22 mL of sulfuryl chloride in 60 mL hexanes, added at a rate that maintained the temperature below $-10°$ C. The reaction mixture was then stirred at room temperature for one hour. The precipitated solids were collected, washed with ether and water, and dried to afford 26 g of 3-chloro-2-(N,N-dimethylsulfamoyl)benzenesulfonyl chloride as a yellow solid, which was used without further purification; IR (KBr): 1375, 1350, 1180 and 1160 cm$^{-1}$.

EXAMPLE 3

3-Chloro-N,N-dimethyl-1,2-benzenedisulfonamide

A stirred solution of 26 g of 3-chloro-2-(N,N-dimethylsulfamoyl)benzenesulfonyl chloride in 300 mL tetrahydrofuran was cooled to about 0° C. and treated with liquid ammonia at a rate that kept the temperature below 10° C. When the addition was complete, the reaction mixture was allowed to warm to room temperature and was stirred for 4 hours. The precipitate was removed by filtration, washed well with tetrahydrofuran, and the combined filtrates were evaporated in vacuo to afford a solid, which was triturated with water and dried to give 23.5 g of 3-chloro-N,N-dimethyl-1,2-benzenedisulfonamide as a yellow solid, m.p. 171°–182° C.; NMR ($CDCl_3/DMSO$-$d_6$): $\delta 3.0$ (s, 6H), 7.6–7.9 (m, 2H), 8.45 (dd, 1H); IR (KBr): 3460, 3360, 3250, 1355, 1325, 1170, 1150 cm$^{-1}$.

EXAMPLE 4

N'-Butylaminocarbonyl-3-chloro-N,N-dimethyl-1,2-benzenedisulfonamide

To 140 mL of methyl ethyl ketone was added 14.3 g of 3-chloro-N,N-dimethyl-1,2-benzenedisulfonamide, 7.2 g of potassium carbonate and 7.5 ml of n-butyl isocyanate. This mixture was heated at reflux temperature for 3 hours, cooled to room temperature, poured into 1500 mL of ice water, and acidified to pH 1 with concentrated hydrochloric acid. The resulting precipitate was collected, washed with water, and dried to afford 17.4 g of N'-butylaminocarbonyl-3-chloro-N,N-dimethyl-1,2-benzenedisulfonamide as a white powder, m.p. 107°–115° C.; NMR ($CDCl_3$): $\delta 0.9$ (br t, 3H), 1.2–1.7 (m, 4H), 3.0 (s, 6H), 3.3–3.4 (m, 2H), 6.6 (t, 1H), 7.6–8.0 (m, 2H), 8.5 (dd, 1H), 9.0 (br s, 1H).

EXAMPLE 5

2,3-Dichlorobenzenesulfonyl chloride

To a stirred solution of 70.0 g of 2,3-dichloroaniline in 51 mL of acetic acid was added 180 mL of concentrated hydrochloric acid portionwise. External cooling was used to maintain the temperature below 50° C. To this thick mixture at $-5°$ C. was added a solution of 37.0 g of sodium nitrite in 80 mL of water dropwise at a rate that maintained the temperature below 50° C. After the addition was complete, the cloudy mixture was stirred at 0° C. for 10 minutes, and was then poured slowly into a suspension of 500 mL of acetic acid, 150 mL of sulfur dioxide and 10 g of cupric chloride dihydrate at 10°–20° C. Moderate gas evolution with excessive foaming occurred, but subsided after approximately ten minutes. This light brown mixture was stirred at ambient temperature for 1–1.5 hours and was then poured into 2 L of ice water with stirring. The resultant light brown precipitate was filtered, washed twice with 200 mL portions of water, and dried to yield 110 g of 2,3-dichlorobenzenesulfonyl chloride as a light brown solid, m.p. 56°–58° C., which was used without further purification; IR (nujol): 1375, 1175 cm$^{-1}$.

EXAMPLE 6
2,3-Dichlorobenzenesulfonamide

To a stirred solution of 60.0 g of 2,3-dichlorobenzenesulfonyl chloride in 500 mL of tetrahydrofuran at 0° C. was added 30 mL of concentrated ammonium hydroxide (30%) dropwise at a rate that maintained the temperature below 15° C. After an additional stirring period of 0.5 hr, the tetrahydrofuran was evaporated under reduced pressure. The resultant solid residue was triturated with 500 mL of water, filtered, and the collected solid washed twice with 100-mL portions of water and dried to yield 52 g of 2,3-dichlorobenzenesulfonamide as a tan solid, m.p. 210°–226° C.; IR (nujol): 3360, 3250, 1370, 1175, 1165 cm$^{-1}$.

EXAMPLE 7
2,3-Dichlorobenzenesulfonyl isocyanate

To 350 mL of dry xylenes was added 44 g of 2,3-dichlorobenzenesulfonamide, 23 mL of n-butyl isocyanate and 0.3 g 1,4-diazobicyclo[2.2.2]octane. This mixture was heated to reflux (138° C.) under a nitrogen atmosphere. After two hours, liquid phosgene was added to the refluxing mixture in portions over 1.5 hours at such a rate that kept the temperature between 130°–138° C. The phosgene addition was ceased when the reflux temperature had fallen to 130° C. and failed to rise, indicating that consumption of the starting material was complete (13.5 mL phosgene). The mixture was refluxed for an additional hour, cooled to room temperature, and filtered under nitrogen. Evaporation of the filtrate under reduced pressure gave 55 g of crude 2,3-dichlorobenzenesulfonyl isocyanate as a dark oil. This oil was taken up in dry acetonitrile (total solution volume 140 mL) and used as such for subsequent experiments: IR (Neat): 2250 (NCO) cm$^{-1}$

EXAMPLE 8
N-(Cyclopentylaminocarbonyl)-2,3-dichlorobenzenesulfonamide

To 20 mL of the acetonitrile solution containing 2,3-dichlorobenzenesulfonyl isocyanate, prepared as described in the previous example, was added 2.5 mL of cyclopentylamine. This mixture was allowed to sit overnight. The solid precipitate was filtered off and triturated with 5 mL of acetonitrile. Filtration and drying afforded 5.0 g of the title compound as an off-white solid, m.p. 202°–207° C.; NMR (DMSO-d$_6$): δ1.1–1.8 (m, 8H), 3.7 (m, 1H), 6.5 (br d, 1H), 7.6 (t, 1H), 7.9 (dd, 1H), 8.0 (dd, 1H), 10.8 (br s, 1H); IR (nujol): 3343, 1660, 1375, 1170 cm$^{-1}$.

EXAMPLE 9
N-(Aminocarbonyl)-2-chlorobenzenesulfonamide

A solution of 314 g of 2-chlorobenzenesulfonyl isocyanate in 2 L of toluene was cooled to 0° C. and treated with 27 g of anhydrous liquid ammonia, added dropwise at a rate that maintained the temperature around 0° C. After the addition was complete, the reaction mixture was allowed to warm to room temperature. The solids were collected by filtration, and washed with hexane and acetonitrile. The yield of N-(aminocarbonyl)-2-chlorobenzenesulfonamide was 313 g as a white solid, m.p. 160°–163° C.; IR (nujol): 3400, 3300, 1700, 1650, 1550, 1250, 1150 cm$^{-1}$.

EXAMPLE 10
N-(Aminocarbonyl)-2,3-dichlorobenzenesulfonamide

A solution of 10.0 g of 2,3-dichlorobenzenesulfonyl isocyanate in 200 mL of dry tetrahydrofuran was cooled to 0° C. and treated with 5.0 mL of anhydrous liquid ammonia, added in a dropwise manner at a rate that maintained the temperature between 0° and 10° C. The resultant white mixture was allowed to warm to room temperature and was stirred overnight. The precipitate was collected by filtration, dissolved in 250 mL of water, and acidified with concentrated hydrochloric acid to yield a white solid. Filtration and air drying gave 7.0 g of the title compound, m.p. 197°–200° C.; NMR (DMSO-d$_6$): δ6.0–6.8 (br s, 2H), 7.6 (t, 1H), 7.8–8.1 (m, 2H), 11.1 (br s, 1H); IR (nujol): 1690 cm$^{-1}$.

Following the procedures outlined in Equations 1 and 2, and Examples 1–10, one skilled in the art may prepare the compounds of Table 1.

TABLE 1

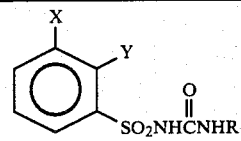

| Antidote Ref. No. | X | Y | R | m.p.(°C.) |
|---|---|---|---|---|
| Ib | H | Cl | H | 169–170 |
| If | H | Cl | CH$_3$ | 153–155 |
|    | H | Cl | CH$_2$CH$_3$ | |
| Ii | Cl | Cl | CH(CH$_3$)$_2$ | 141–164 |
| Ih | Cl | Cl | (CH$_2$)$_3$CH$_3$ | 138–142 |
| Ic | Cl | Cl | H | 198–204 |
|    | Br | Cl | H | |
|    | F | Cl | H | |
| Ij | Cl | Cl | (CH$_2$)$_2$CH$_3$ | 188–192 |
| Id | Cl | Cl | cyclopentyl | 199–201 |
|    | H | Cl | cyclohexyl | |
|    | H | Cl | CH$_2$Ph | |
| Ie | H | Cl | CH$_2$CH$_2$OCH$_3$ | 148–149 |
|    | H | Cl | CH(CH$_3$)CH$_2$OC$_2$H$_5$ | |
|    | H | Cl | (CH$_2$)$_3$CH$_2$SCH$_3$ | |
|    | H | Cl | CH$_2$CH$_2$SC$_2$H$_5$ | |
| Ik | Cl | SO$_2$N(CH$_3$)$_2$ | CH$_2$CH$_3$ | 165–169 |

TABLE 1-continued

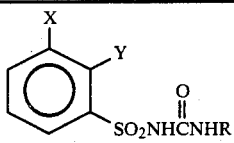

| Antidote Ref. No. | X | Y | R | m.p.(°C.) |
|---|---|---|---|---|
|  | H | SO$_2$N(CH$_3$)$_2$ | CH(CH$_3$)$_2$ |  |
| Ia | Cl | SO$_2$N(CH$_3$)$_2$ | (CH$_2$)$_3$CH$_3$ | 107–115 |
| Il | Cl | SO$_2$N(CH$_3$)$_2$ | (CH$_2$)$_2$CH$_3$ | 166–168 |
|  | Cl | SO$_2$N(CH$_3$)$_2$ | cyclopentyl |  |
|  | Cl | SO$_2$N(CH$_3$)$_2$ | cyclohexyl |  |
|  | Cl | SO$_2$N(CH$_3$)$_2$ | CH$_2$Ph |  |
|  | Cl | SO$_2$N(CH$_3$)$_2$ | CH$_2$CH$_2$OCH$_3$ |  |
|  | Cl | SO$_2$N(CH$_3$)$_2$ | CH(CH$_3$)CH$_2$OC$_2$H$_5$ |  |
|  | Cl | SO$_2$N(CH$_3$)$_2$ | (CH$_2$)$_3$CH$_2$SCH$_3$ |  |
|  | Cl | SO$_2$N(CH$_3$)$_2$ | CH$_2$CH$_2$SC$_2$H$_5$ |  |
| Im | Cl | SO$_2$N(CH$_3$)$_2$ | (CH$_2$)$_3$SCH$_3$ | 131–136 |
|  | Cl | SO$_2$N(CH$_3$)(C$_2$H$_5$) | (CH$_2$)$_3$CH$_3$ |  |
|  | Cl | SO$_2$N(C$_2$H$_5$)$_2$ | (CH$_2$)$_3$CH$_3$ |  |
|  | Br | SO$_2$N(CH$_3$)$_2$ | (CH$_2$)$_3$CH$_3$ |  |
| Ig | F | SO$_2$N(CH$_3$)$_2$ | (CH$_2$)$_3$CH$_3$ | 130–132 |

The herbicides of Formulae II–VIII can be prepared by methods known in the art.

| Compound Number | Reference |
|---|---|
| II, IV, VII | U.S. 4,394,506 |
| III, VI | U.S. 4,383,113 |
| V | U.S. 4,127,405 |
| VIII | EP-A-30,142 |

Formulations

The antidotes described herein can be formulated in a number of ways:

(a) the antidote can be formulated for application directly to the crop seed;

(b) the antidote and herbicide may be formulated separately and applied separately or applied simultaneously in an appropriate weight ratio, e.g., as a tank mix; or (c) the antidote and herbicide may be formulated together in the proper weight ratio.

Useful formulations of the compounds of Formula 1 can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 2

| | Active Ingredient | Weight Percent* | |
|---|---|---|---|
| | | Diluent(s) | Surfactant(s) |
| Wettable Powders | 20–90 | 0–74 | 1–10 |
| Oil Suspensions Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June, 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 11

| Wettable Powder | |
|---|---|
| N—(cyclopentylaminocarbonyl)-2,3-dichlorobenzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 12

| Wettable Powder | |
|---|---|
| N—(aminocarbonyl)-2-chlorobenzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 13

| Granule | |
|---|---|
| Wettable Powder of Example 12 | 5% |
| attapulgite granules (U.S.S. 20-40 mesh; 0.84–0.42 mm) | 95% |

A slurry of wettable powder containing 25% solids is sprayed on the surface of attapulgite granules in a double-cone blender. The granules are dried and packaged.

EXAMPLE 14

| Extruded Pellet | |
|---|---|
| N'—butylaminocarbonyl-3-chloro-N,N—dimethyl-1,2-benzenedisulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 15

| Oil Suspension | |
|---|---|
| N—(aminocarbonyl)-2,3-dichlorobenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

| Wettable powder | |
|---|---|
| N'—butylaminocarbonyl-3-chloro-N,N—dimethyl-1,2-benzenedisulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 17

| Low Strength Granule | |
|---|---|
| N'—butylaminocarbonyl-3-chloro-N,N—dimethyl-1,2-benzenedisulfonamide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 18

| Aqueous Suspension | |
|---|---|
| N—(aminocarbonyl)-2-chlorobenzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 19

| Solution | |
|---|---|
| N'—butylaminocarbonyl-3-chloro-N,N—dimethyl-1,2-benzenedisulfonamide | 5% |
| water | 95% |

The salt is added directly to the water with stirring to produce the solution, which may then be packaged for use.

EXAMPLE 20

| Low Strength Granule | |
|---|---|
| N'—butylaminocarbonyl-3-chloro-N,N—dimethyl-1,2-benzenedisulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 21

| Granule | |
|---|---|
| N—(cyclopentylaminocarbonyl)-2,3-dichloro-benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 22

| High Strength Concentrate | |
|---|---|
| N—(cyclopentylaminocarbonyl)-2,3-dichloro-benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 23

| Wettable Powder | |
|---|---|
| N—(aminocarbonyl)-2,3-dichloro-benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 24

| Wettable Powder | |
|---|---|
| N—butylaminocarbonyl-3-chloro-N,N—dimethyl-1,2-benzenedisulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 25

| Oil Suspension | |
|---|---|
| N'—butylaminocarbonyl-3-chloro-N,N—dimethyl-1,2-benzenedisulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 26

| Slurry Seed Coat | |
|---|---|
| N'—butylaminocarbonyl-3-chloro-N,N—dimethyl-1,2-benzenedisulfonamide | 65% |
| calcium ligninsulfonate | 4% |
| trimethyl nonyl polyethylene glycol ether | 4% |
| Rhodamine B | 1% |
| permanent red 2 B, calcium salt, extended on Blanc Fixe | 1% |
| diatomaceous earth | 25% |

The liquid surfactant is sprayed on the diatomaceous earth, the other ingredients are then added and thoroughly mixed together in an efficient blender. The mixture is then coarsely hammer-milled and passed through a fluid mill to produce particles of active ingredient that are essentially all less than 10 microns in diameter. The product is reblended before packaging. (Product is used by making about a 30–40% slurry in water and applying the slurry to seed in a commercial seed treater.)

EXAMPLE 27

| Dust Seed Coat | |
|---|---|
| N—(cyclopentylaminocarbonyl)-2,3-dichloro-benzenesulfonamide | 75% |
| permanent red 2 B, calcium salt, extended on Blanc Fixe | 5% |
| diatomaceous earth | 20% |

The ingredients are blended, coarsely hammer-milled and passed through a fluid mill to produce particles of active ingredient that are essentially all below 10 microns in diameter. The product is reblended before packaging. (Product is used by dusting on seed at rates of 1–800 gms/100 kg.)

Utility

The compounds of Formula I are useful for protecting crop plants from injury due to herbicides of Formulae II-VIII. Protection is achieved by combining the application of the herbicide to the locus of the plant with the application of a non-phytotoxic, antidotally-effective amount of the compounds of Formula I, preferably to the crop seed.

The compounds of Formula I can eliminate, or reduce to an acceptable level, injury caused by herbicides to cereal crops such as corn, sorghum, wheat and barley.

A number of methods are available for combining the application of the herbicidal and antidotal compounds described herein. The antidotes may be applied directly to the crop seed. The seeds may be uniformly coated with the antidote according to standard seed treating procedures prior to planting. Alternatively, the antidote may be applied over the exposed seed in open furrows at planting, just prior to covering the seed with soil (in-the-furrow treatment). The herbicide may be applied post-emergence (applied to emerged crop and/or weeds and on the exposed soil surface). In addition, the antidote and herbicides may be applied postemergence. Post-emergence treatments may be directed so that the antidote and/or herbicide is applied primarily to the crop or weeds.

The ratio of antidote to herbicide used will vary, depending upon the specific antidote and herbicide used and upon the method of application used. The crop species and cultural practices may also have an effect. For example, when the antidote is applied as a seed coating, it may be applied at a rate of about 0.1 to 0.5% of the seed weight. When the seeds are planted at from 10 to 150 kg/ha, the antidote would be distributed at from 0.01 to 0.75 kg/ha. In the most postemergence treatment, the antidote may be applied at about 0.1 to 10 kg/ha. Similar rates may be used for in-the-furrow treatments; however, since only the furrow is treated, the lower per hectare rate would be diminished to as low as 0.01 kg/ha, depending upon the row spacing. Since the herbicides may be used at rates of about 0.001 to 2 kg/ha, the ratio of herbicide to antidote may vary between 1:200 to 1:10,000. One skilled in the art can determine the proper ratio to use in a given situation.

Antidote Protection by Seed Treatment

Corn and sorghum seeds were coated with antidotes to obtain 0.1 to 0.5% of seed weight. Known weights of seed and antidote were placed in a glass jar, a few drops of water or 1% methanol added, and the jar was shaken until the seeds appeared evenly coated. After the seeds had been aerated thoroughly, they were planted in Terra-Lite Metro-Mix Growing Medium* or steam-sterilized soil/Terra-Lite Metro-Mix (350) Growing Medium. Untreated weed seeds were also similarly planted. The pots were watered with tap water and fertilized with Peters ® Fertilizer. The herbicide treatments were made preemergence or to the seedlings at the 2-4 leaf stages by foliar spray. Solutions of the herbicides were made up in water-surfactant carrier or acetone-water-surfactant. The tests were held in the greenhouse under standard greenhouse care until evaluation was made 10-28 days after herbicide treatment (DAT). The degree of antidote protection was rated by visual evaluation. Herbicide injury was visually rated on a scale of 0 to 10 in which 0 indicated no injury and 10 indicated that the plants were dead. The type of response is indicated by letters where:

G = growth retardation; and
H = hormonal effect.

In some istances plant height was used to measure chemical effects. The results are given in Tables 3-13.
*The Terra-Lite Metro-Mix Growing Medium manufactured by Grace & Co., Cambridge, Mass.

TABLE 3

| | Sorghum Injury | | |
|---|---|---|---|
| Antidote | Untreated Check Height (cm) | V Treated Check Height (cm) | Antidote Treated + V Treated Height (cm) |
| | Test I | | |
| Ia | 21 | 8 | 20 |
| | Test II | | |
| Ia | 40 | 10 | 31 |
| Ig | 40 | 10 | 23 |
| Ih | 40 | 10 | 12 |
| Ic | 40 | 10 | 28 |
| Ii | 40 | 10 | 24 |
| Ij | 40 | 10 | 20 |

TABLE 4

| Antidote | Rate (% SW*) | Plant Injury Rating + VIII (32 g/ha) Corn | Sorghum |
|---|---|---|---|
| None | 0 | 8G | 9G |
| Ia | 0.3% | 8G | 5G |
| Ib | 0.3% | 2G | 5G |
| Ie | 0.3% | 2G | — |

*% SW = percent seed weight

TABLE 5

| | | Plant Injury Rating 19 DAT | | | | | |
|---|---|---|---|---|---|---|---|---|
| Herbicide | Rate (g/ha) | Corn Antidote None | + Ib 0.3% SW* | Giant Foxtail | Crab-grass | Shatter-cane | Barnyard-grass | Johnson-grass |
| VIII | 32 | 7G | 0 | 0 | 0 | 3G | 0 | 0 |

*% SW = percent seed weight

TABLE 6

| Antidote | Rate (% SW*) | Plant Injury Ratings 26 DAT + VIII (32 g/ha) Corn |
|---|---|---|
| None | 0 | 7G,8H |
| Ia | 0.3% | 5G,6H |
| Ib | 0.3% | 0 |
| Ic | 0.3% | 0 |
| If | 0.3% | 0 |

*% SW = percent seed weight

TABLE 7

Corn Injury Rating 17 DAT

| Herbi-cide | Rate (g/ha) | None | Antidote Ib 0.3% SW* | Ic 0.3% SW* | Id 0.3% SW* |
|---|---|---|---|---|---|
| VIII | 32 | 2G,4H | 2G | 0 | 2G |
|  | 8 | 1G | 1G | 0 | 1G |
| None |  | 0 | 0 | 0 | 0 |

*% SW = percent seed weight

TABLE 8

Sorghum Plant Injury Ratings 17 DAT

| Herbi-cide | Rate (g/ha) | None | Antidote + Ib 0.3% SW* | + Ic 0.3% SW* | + Id 0.3% SW* |
|---|---|---|---|---|---|
| VIII | 32 | 8G,8H | 3G | 1G | 1G |
|  | 8 | 4G,6H | 1G | 0 | 0 |
| None |  | 0 | 0 |  |  |

*% SW = percent seed weight

TABLE 9

Plant Injury Rating 30 DAT

| Herb-icide | Rate (g/ha) | None | Corn Antidote Ia 0.3% SW* | Ib 0.3% SW | Ic 0.3% SW | Lambs-quarters | Velvet-leaf | Pig-weed | Cockle-bur | Morning-glory |
|---|---|---|---|---|---|---|---|---|---|---|
| VIII | 32 | 7G | 4G | 1G | 0 | 10G | 10G | 10G | 10G | 9G |
|  | 16 | 2G | 1G | 0 | 0 | 10G | 8G | 10G | 10G | 6G,6H |
|  | 8 | 1G | 0 | 0 | 0 | 10G | 6G | 10G | 7G | 4G |
| None |  | 0 | 0 | 0 | 0 | 0 | 0 | 0 | 0 | 0 |

*% SW = percent seed weight

TABLE 10

Corn Response When Treated with VIII 19 DAT

| Antidote | Rate (% SW*) | 32 (g/ha) | 16 (g/ha) | 8 (g/ha) |
|---|---|---|---|---|
| None | 0 | 6G,8H | 4G,6H | 1G |
| Ia | 0.25% | 2G | 1G | 1G |
| Ib | 0.25% | 1G | 0 | 0 |
| Ic | 0.25% | 1G | 0 | 0 |

*% SW = percent seed weight

TABLE 11

Corn Response 24 DAT

| Herbi-cide | Rate (g/ha) | None | + Ia .25% SW* | + Ia .50% | + Ib .25% SW* | + Ib .50% | + Ic .25% SW* | + Ic .50% |
|---|---|---|---|---|---|---|---|---|
| VIII | 32 | 7G | 4G | 3G | 0 | 1G | 0 | 0 |
|  | 16 | 2G | 1G | 1G | 0 | 1G | 0 | 0 |
| V | 8 | 10G | 6G,4H | 6G,4H | 1G | 1G | 0 | 0 |
| II | 16 | 4G | 2G | 2G | 1G | 1G | 0 | 0 |
| None |  | 0 | 0 | 0 | 0 | 0 | 0 | 0 |

*% SW = percent seed weight

TABLE 12

Plant Injury Rating When Treated With VIII 19 DAT

| Rate (g/ha) | None | Corn Antidote + Ia .25% SW* | + Ib .25% | + Ic .25% |
|---|---|---|---|---|
| 32 | 6G,8H | 2G | 1G | 1G |
| 16 | 4G,6H | 1G | 0 | 0 |
| 8 | 1G | 1G | 0 | 0 |
|  | 0 | 0 | 0 | 0 |
| Pigweed | 10G | 10G | 10G | 0 |
| Cocklebur | 10G | 10G | 8G | 0 |
| Pitted Morningglory | 10G | 10G | 8G | 0 |
| Velvetleaf | 10G | 10G | 10G | 0 |
| Lambs-quarters | 10G | 10G | 10G | 0 |
| Giant Foxtail | 0 | 0 | 0 | 0 |
| Yellow Foxtail | 0 | 0 | 0 | 0 |
| Shattercane | 0 | 0 | 0 | 0 |
| Wild Proso millet | 0 | 0 | 0 | 0 |
| Johnsongrass | 0 | 0 | 0 | 0 |
| Brown top millet | 0 | 0 | 0 | 0 |

*% SW = percent seed weight

TABLE 13

Plant Injury Rating 21 DAT

| Treat-ment | Rate (g/ha) | None | Corn Antidote + Ia 0.25% SW* | + Ib 0.25% SW | + Ic 0.25% SW | Amsoy 71 | Lambs-quarters | Cockle-bur | Velvet-leaf | Morning-glory |
|---|---|---|---|---|---|---|---|---|---|---|
| VIII | 32 | 8G | 8G | 3G | 2G | 5G | 10G | 10G | 10G | 9G |
|  | 16 | 6G | 4G | 1G | 0 | 6G | 10G | 10G | 10G | 9G |
|  | 8 | 4G | 1G | 0 | 0 | 5G | 10G | 10G | 10G | 8G |
|  | 4 | 1G | 1G | 0 | 0 | 1G | 10G | 7G | 8G | 6G |
|  | 2.5 | 0 | 0 | 0 | 0 | 0 | 8G | 6G | 7G | 5G |
|  | 1 | 0 | 0 | 0 | 0 | 0 | 8G | 1G | 3G | 1G |

TABLE 13-continued

| | | Plant Injury Rating 21 DAT | | | | | | | | |
|---|---|---|---|---|---|---|---|---|---|---|
| | | | Corn Antidote | | | | | | | |
| Treatment | Rate (g/ha) | None | + Ia 0.25% SW* | + Ib 0.25% SW | + Ic 0.25% SW | Amsoy 71 | Lambsquarters | Cocklebur | Velvetleaf | Morningglory |
| II | 8 | 4G | 3G | 1G | 1G | 0 | 0 | 10G | 8G | 9G |
| | 4 | 3G | 1G | 0 | 0 | 0 | 0 | 10G | 6G | 9G |
| | 2 | 1G | 0 | 0 | 0 | 0 | 0 | 8G | 4G | 8G |
| Check | 0 | 0 | 0 | 0 | 0 | 0 | 0 | 0 | 0 | 0 |

*% SW = percent seed weight

Postemergence Herbicide Antidote Tests

Cereal crop plants, corn and sorghum and the weeds used in the tests, were grown in pots in Metro-mix or steam-sterilized soil/Metro-mix in the greenhouse. The pots were watered with tapwater and fertilized with Peters® fertilizer. The herbicide/antidote treatments were made on seedlings at the 2–4 leaf stages by a foliar spray. Solutions of the herbicide and antidote were made up separately or together in either water-surfactant carrier or acetone-water-surfactant carrier. Applications of the herbicide and antidote were made sequentially or tank-mix.

Evaluation of the antidote action was made 14–28 days after the postemergence treatment (DAT). The degree of antidote protection was rated by visual measurement and shoot fresh weight measurement. Where shoot fresh weight was recorded, the herbicide injury and/or antidoting was computed as percent of check plant shoot fresh weight. Herbicide injury was visually rated on a scale of 0 to 10 in which 0 indicated no injury and 10 indicated that the plants were dead. The results are given in Tables 14–31.

TABLE 14

| V + Antidote | Sorghum Rating |
|---|---|
| Ia | 1 |
| Ig | 3 |
| Ih | 1 |
| Ic | 1 |
| Ii | 1 |
| Ij | 3 |
| Ik | 4 |
| Il | 5 |
| Im | 5 |
| None | 8 |

TABLE 15

| | | Plant Injury Ratings 25 DAT + VIII (250 g/ha) | | | |
|---|---|---|---|---|---|
| Antidote | Rate (g/ha) | Corn | Sorghum | Rape | Wild Mustard |
| Ia | 1000 | 10G | 8G | 10G | 10G |
| Ib | 250 | 0 | 3G | 10G | 10G |
| None | 0 | 10G | 10G | 10G | 10G |

TABLE 16

| | | Corn Injury Rating 24 DAT + VIII | |
|---|---|---|---|
| Antidote | Rate (g/ha) | 125 (g/ha) | 64 (g/ha) |
| Ia | 1000 | 9G | 6G,8H |
| | 250 | 10G | 8G |
| Ib | 1000 | 0 | 0 |
| | 250 | 0 | 0 |

TABLE 16-continued

| | | Corn Injury Rating 24 DAT + VIII | |
|---|---|---|---|
| Antidote | Rate (g/ha) | 125 (g/ha) | 64 (g/ha) |
| None | 0 | 10G | 10G |

TABLE 17

| | | Plant Injury Rating DAT + VIII (32 g/ha) | | |
|---|---|---|---|---|
| Antidote | Rate (g/ha) | Corn | Velvetleaf | Cocklebur |
| Ib | 1000 | 1G | 10G | 10G |
| | 250 | 0 | 10G | 10G |
| | 64 | 0 | 10G | 10G |
| None | 0 | 7G,6H | 10G | 10G |

TABLE 18

| | | Plant Injury Rating 17 DAT + VIII (32 g/ha) | | | | | |
|---|---|---|---|---|---|---|---|
| Antidote | Rate (g/ha) | Wheat | Corn | Sorghum | Shattercane | Green Foxtail | Wild Oats |
| Ib | 250 | 0 | 0 | 0 | 0 | 0 | 0 |
| Ia | 250 | 0 | 7G | 0 | 0 | 0 | 0 |
| None | 0 | 0 | 6G,6H | 7G,8H | 1G | 0 | 0 |

TABLE 19

| | | Plant Injury Rating 30 DAT | | | | | |
|---|---|---|---|---|---|---|---|
| Antidote | Rate (g/ha) | Corn | Lambsquarters | Pigweed | Velvetleaf | Cocklebur | Morningglory Mixed |
| | | + VIII (32 g/ha) | | | | | |
| None | 0 | 6G,6H | 10G | 10G | 10G | 10G | 9G |
| Ia | 500 | 4G | 10G | 10G | 10G | 10G | 9G |
| | 250 | 2g,6H | 10G | 10G | 10G | 10G | 9G |
| | 125 | 3G,6H | 10G | 10G | 10G | 10G | 9G |
| | 64 | 4G,6H | 10G | 10G | 10G | 10G | 9G |
| Ib | 500 | 1G | 10G | 10G | 10G | 10G | 9G |
| | 250 | 1G | 10G | 10G | 10G | 10G | 9G |
| | 125 | 1G | 10G | 10G | 10G | 10G | 9G |
| | 64 | 2G | 10G | 10G | 10G | 10G | 9G |
| Ic | 500 | 3G | 10G | 10G | 10G | 10G | 9G |
| | 250 | 1G | 10G | 10G | 10G | 10G | 9G |
| | 125 | 1G | 10G | 10G | 10G | 10G | 9G |
| | 64 | 2G | 10G | 10G | 10G | 10G | 9G |
| | | + VIII (16 g/ha) | | | | | |
| None | 0 | 2G | 10G | 10G | 10G | 10G | 4G |
| Ia | 250 | 0 | 10G | 10G | 10G | 10G | 3G |
| | 125 | 0 | 10G | 10G | 10G | 10G | 3G |
| | 64 | 0 | 10G | 10G | 10G | 10G | 3G |
| | 32 | 0 | 10G | 10G | 10G | 10G | 3G |
| Ib | 250 | 0 | 10G | 10G | 10G | 10G | 3G |
| | 125 | 0 | 10G | 10G | 10G | 10G | 3G |
| | 64 | 10G | 10G | 10G | 10G | 3G | |
| | 32 | 0 | 10G | 10G | 10G | 10G | 3G |
| Ic | 250 | 0 | 10G | 10G | 10G | 10G | 3G |
| | 125 | 0 | 10G | 10G | 10G | 10G | 3G |

TABLE 19-continued

| | | Plant Injury Rating 30 DAT | | | | |
|---|---|---|---|---|---|---|
| Antidote | Rate (g/ha) | Corn | Lambsquarters | Pigweed | Velvetleaf | Cocklebur | Morning glory Mixed |
| | 64 | 0 | 10G | 10G | 10G | 10G | 3G |
| | 32 | 0 | 10G | 10G | 10G | 10G | 3G |

TABLE 20

| | | Plant Injury Rating 19 DAT | | | | | | | | | | | |
|---|---|---|---|---|---|---|---|---|---|---|---|---|---|
| Antidote | Rate (g/ha) | Corn | Pigweed | Cocklebur | Pitted Morningglory | Velvetleaf | Lambsquarters | Giant Foxtail | Yellow Foxtail | Shattercane | Proso Millet | Johnsongrass | Brown Top Millet |
| | | | | | + VIII (32 g/ha) | | | | | | | | |
| None | 0 | 6G,8H | 10G | 10G | 10G | 10G | 10G | 0 | 0 | 0 | 0 | 0 | 0 |
| Ic | 500 | 1G | 10G | 10G | 10G | 10G | 10G | 0 | 0 | 0 | 0 | 0 | 0 |
| | 250 | 1G | 10G | 10G | 10G | 10G | 10G | 0 | 0 | 0 | 0 | 0 | 0 |
| | 125 | 1G | 10G | 10G | 10G | 10G | 10G | 0 | 0 | 0 | 0 | 0 | 0 |
| | | | | | + VIII (16 g/ha) | | | | | | | | |
| None | 0 | 4G,6H | 10G | 10G | 10G | 10G | 10G | 0 | 0 | 0 | 0 | 0 | 0 |
| Ic | 250 | 0 | 10G | 10G | 10G | 10G | 10G | 0 | 0 | 0 | 0 | 0 | 0 |
| | 125 | 0 | 10G | 10G | 10G | 10G | 10G | 0 | 0 | 0 | 0 | 0 | 0 |
| | 64 | 1G | 10G | 10G | 10G | 10G | 10G | 0 | 0 | 0 | 0 | 0 | 0 |
| | | | | | + VIII (8 g/ha) | | | | | | | | |
| None | 0 | 1G | 10G | 8G | 8G | 10G | 10G | 0 | 0 | 0 | 0 | 0 | 0 |
| Ic | 125 | 0 | 10G | 10G | 9G | 10G | 10G | 0 | 0 | 0 | 0 | 0 | 0 |
| | 64 | 0 | 10G | 9G | 9G | 10G | 10G | 0 | 0 | 0 | 0 | 0 | 0 |
| | 32 | 0 | 10G | 9G | 9G | 10G | 10G | 0 | 0 | 0 | 0 | 0 | 0 |

TABLE 21

| Treatment | Rate (g/ha) | Plant Response 26 DAT | | |
|---|---|---|---|---|
| | | Corn | Lambsquarters | Pigweed |
| VIII | 16 | 3G | 10G | 10G |
| + Ib | 16 + 16 | 2G | 10G | 10G |
| | 16 + 32 | 0 | 10G | 10G |
| | 16 + 64 | 0 | 10G | 10G |
| | 16 + 125 | 0 | 10G | 10G |
| + Ic | 16 + 16 | 1G | 10G | 10G |
| | 16 + 32 | 0 | 10G | 10G |
| | 16 + 64 | 0 | 10G | 10G |
| | 16 + 125 | 0 | 10G | 10G |
| None | 0 | 0 | 0 | 0 |

TABLE 22

| Treatment | Rate (g/ha) | Plant Response 26 DAT | | |
|---|---|---|---|---|
| | | Corn | Lambsquaters | Pigweed |
| VIII | 32 | 5G,6H | 10G | 10G |
| + Ib | 32 + 32 | 4G | 10G | 10G |
| | 32 + 64 | 2G | 10G | 10G |
| | 32 + 125 | 1G | 10G | 10G |
| | 32 + 250 | 0 | 10G | 10G |
| + Ic | 32 + 32 | 2G | 10G | 10G |
| | 32 + 64 | 1G | 10G | 10G |
| | 32 + 125 | 0 | 10G | 10G |
| | 32 + 250 | 0 | 10G | 10G |
| None | 0 | 0 | 0 | 0 |

TABLE 23

| Antidote | Rate (g/ha) | Plant Injury Ratings 25 DAT + VI (125 g/ha) | | | |
|---|---|---|---|---|---|
| | | Corn | Sorghum | Rape | Wild Mustard |
| Ia | 1000 | 8G | 9G | 10G | 10G |
| Ib | 250 | 2G | 2G | 10G | 10G |
| None | 0 | 10G | 10G | 10G | 10G |

TABLE 24

| Treatment | Rate (g/ha) | Plant Response 26 DAT | | |
|---|---|---|---|---|
| | | Corn | Lambsquarters | Pigweed |
| VI | 16 | 6G,4H | 10G | 9G |
| + Ib | 16 + 250 | 0 | 10G | 0 |
| + Ic | 16 + 250 | 0 | 0 | 0 |
| VI | 32 | 10G | 10G | 10G |
| + Ib | 32 + 250 | 0 | 10G | 0 |
| + Ic | 32 + 250 | 0 | 6G | 0 |

TABLE 25

| | | Corn Injury Rating Shoot Fresh Weight (% check) Herbicides | | |
|---|---|---|---|---|
| Antidote | Rate (g/ha) | + VIII 16 g/ha | + V 32 g/ha | + II 16 g/ha |
| None | — | 62 | 0 | 94 |
| Ib | 1000 | 70 | 36 | 65 |
| | 250 | 96 | 0 | 67 |
| Ie | 1000 | 90 | 12 | 94 |
| | 250 | 74 | 0 | 86 |
| If | 1000 | 78 | 40 | 82 |
| | 250 | 87 | 67 | 77 |
| None | — | 0 | 0 | 0 | 0 |

TABLE 26

| | | Barley Injury Rating Shoot Fresh Weight (% check) Herbicides | | |
|---|---|---|---|---|
| Antidote | Rate (g/ha) | + IV 64 g/ha | + III 125 g/ha | + V 64 g/ha |
| None | — | 31 | 35 | 86 |
| Ib | 1000 | 62 | 53 | 86 |
| | 250 | 34 | 40 | 75 |
| | 64 | 32 | 37 | 70 |
| Ie | 1000 | 36 | 58 | 106 |
| | 250 | 32 | 43 | 77 |
| | 64 | 34 | 42 | 90 |
| If | 1000 | 55 | 61 | 87 |
| | 250 | 51 | 62 | 102 |
| | 64 | 20 | 46 | 66 |

TABLE 27

| Treatment | Rate (g/ha) | Plant Injury Rating 26 DAT Corn |
|---|---|---|
| VIII | 32 | 6G,6H |
| + Ia | 32 + 125 | 6G,6H |
| | 32 + 64 | 6G,6H |
| + Ib | 32 + 125 | 0 |
| | 32 + 64 | 0 |

TABLE 27-continued

| Treatment | Rate (g/ha) | Plant Injury Rating 26 DAT Corn |
|---|---|---|
| + Ic | 32 + 125 | 0 |
|  | 32 + 64 | 0 |
| II | 32 | 3G |
| + Ia | 32 + 125 | 1G |
|  | 32 + 64 | 1G |
| + Ib | 32 + 125 | 0 |
|  | 32 + 64 | 0 |
| + Ic | 32 + 125 | 0 |
|  | 32 + 64 | 0 |
| None | 0 | 0 |

TABLE 28

| | | Plant Injury Rating 19 DAT | | | | | | | | | | |
|---|---|---|---|---|---|---|---|---|---|---|---|---|
| Treatment | Rate (g/ha) | Corn | Pigweed | Cocklebur | Pitted Morningglory | Velvetleaf | Lambsquarters | Giant Foxtail | Yellow Foxtail | Shattercane | Wild Proso millet | Johnsongrass | Brown top millet |
| VIII | 32 | 6G,8H | 10G | 10G | 10G | 10G | 10G | 0 | 0 | 0 | 0 | 0 | 0 |
|  | 16 | 4G,6H | 10G | 10G | 10G | 10G | 10G | 0 | 0 | 0 | 0 | 0 | 0 |
|  | 8 | 1G | 10G | 8G | 8G | 10G | 10G | 0 | 0 | 0 | 0 | 0 | 0 |
| + Ic | 32 + 500 | 1G | 10G | 10G | 10G | 10G | 10G | 0 | 0 | 0 | 0 | 0 | 0 |
|  | 32 + 250 | 1G | 10G | 10G | 10G | 10G | 10G | 0 | 0 | 0 | 0 | 0 | 0 |
|  | 32 + 125 | 1G | 10G | 10G | 10G | 10G | 10G | 0 | 0 | 0 | 0 | 0 | 0 |
|  | 16 + 250 | 0 | 10G | 10G | 10G | 10G | 10G | 0 | 0 | 0 | 0 | 0 | 0 |
|  | 16 + 125 | 0 | 10G | 10G | 10G | 10G | 10G | 0 | 0 | 0 | 0 | 0 | 0 |
|  | 16 + 64 | 0 | 10G | 10G | 10G | 10G | 10G | 0 | 0 | 0 | 0 | 0 | 0 |
|  | 8 + 125 | 0 | 10G | 10G | 9G | 10G | 10G | 0 | 0 | 0 | 0 | 0 | 0 |
|  | 8 + 64 | 0 | 10G | 9G | 9G | 10G | 10G | 0 | 0 | 0 | 0 | 0 | 0 |
|  | 8 + 32 | 0 | 10G | 9G | 9G | 10G | 10G | 0 | 0 | 0 | 0 | 0 | 0 |
| None | 0 | 0 | 0 | 0 | 0 | 0 | 0 | 0 | 0 | 0 | 0 | 0 | 0 |

TABLE 29

| | | Plant Injury Rating 32 DAT | | | | | |
|---|---|---|---|---|---|---|---|
| Treatment | Rate (g/ha) | Corn | Pigweed | Cocklebur | Lambsquarters | Velvetleaf | Pitted Morningglory |
| VIII | 32 | 8H | 10G | 10G | 10G | 10G | 10G |
| + Ib | 32 + 250 | 2G,2H | 10G | 10G | 10G | 10G | 10G |
| + Ic | 32 + 250 | 1G | 10G | 10G | 10G | 10G | 10G |
| V | 4 | 10G | 0 | 10G | 9G | 4G |
| + Ib | 4 + 250 | 2G,2H | 10G | 0 | 9G | 10G | 6G |
| + Ic | 4 + 250 | 1G | 10G | 0 | 10G | 10G | 6G |
| None | 0 | 0 | 0 | 0 | 0 | 0 | 0 |

TABLE 30

| | | Plant Injury Rating 32 DAT | | | | | |
|---|---|---|---|---|---|---|---|
| Treatment | Rate (g/ha) | Corn | Pigweed | Cocklebur | Lambsquarters | Velvetleaf | Pitted Morningglory |
| VI | 32 | 9G | 8G | 10G | 10G | 10G | 8G |
|  | 16 | 5G,4H | 6G,4H | 6G,6H | 10G | 10G | 7G,8H |
|  | 8 | 1G | 4G,6H | 2G,4H | 9G | 9G | 7G,8H |
| + Ib | 32 + 250 | 0 | 6G | 4G,6H | 10G | 9G | 8G,8H |
|  | 16 + 250 | 0 | 2G | 4G | 7G | 7G | 7G,6H |
|  | 8 + 250 | 0 | 1G | 2G | 6G | 5G | 8G,6H |
| + Ic | 32 + 250 | 0 | 8G | 10G | 10G | 10G | 10G |
|  | 16 + 250 | 0 | 6G | 6G,6H | 10G | 4G | 7G,6H |
|  | 8 + 250 | 0 | 0 | 0 | 2G | 1G | 7G,6H |

TABLE 30-continued

| | | Plant Injury Rating 32 DAT | | | | | |
|---|---|---|---|---|---|---|---|
| Treatment | Rate (g/ha) | Corn | Pigweed | Cocklebur | Lambsquarters | Velvetleaf | Pitted Morningglory |
| None | 0 | 0 | 0 | 0 | 0 | 0 |

TABLE 31

| | | Plant Response 28 DAT | | | | | | | | | |
|---|---|---|---|---|---|---|---|---|---|---|---|
| Treatment | Rate (g/ha) | Bonanza | Custer | Glenn | Igri | Klages | Manker | Morex | Park | Sonja | Viva |
| III | 125 | 6G | 7G | 8G | 8G | 6G | 8G | 4G | 6G | 6G | 4G |
| + Ib | 125 + 500 | 0 | 0 | 0 | 0 | 0 | 0 | 0 | 0 | 0 | 0 |
|  | 125 + 375 | 0 | 0 | 0 | 0 | 0 | 0 | 0 | 0 | 0 | 0 |
|  | 125 + 250 | 1G | 1G | 1G | 1G | 1G | 1G | 1G | 1G | 1G | 1G |
|  | 125 + 125 | 1G | 2G | 2G | 4G | 2G | 3G | 1G | 2G | 2G | 2G |
| None | 0 | 0 | 0 | 0 | 0 | 0 | 0 | 0 | 0 | 0 | 0 |

What is claimed is:

1. A herbicidal composition consisting essentially of an antidotally-effective amount of a compound of Formula I, or its agriculturally suitable salt

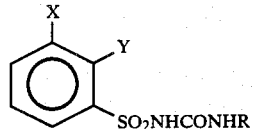

wherein
X is H, Cl, F or Br;
Y is Cl or $SO_2NR^1R^2$;
R is H, $C_1-C_6$ alkyl, $C_5-C_6$ cycloalkyl, or $C_2-C_4$ alkyl substituted with $C_1-C_2$ alkoxy or $C_1-C_2$ alkylthio;
$R^1$ and $R^2$ are independently $C_1-C_2$ alkyl; provided that when Y is $SO_2NR^1R^2$, R is other than H or $CH_3$, and a sulfonylurea herbicide of the formula

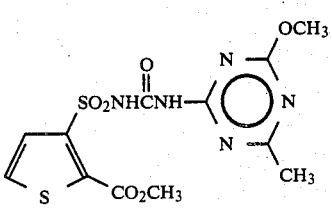

2. The composition of claim 1 wherein in the compound of Formula I, X is H or Cl, Y is Cl or SO$_2$N(CH$_3$)$_2$ and R is H, C$_1$–C$_6$ alkyl or C$_5$–C$_6$ cycloalkyl.

3. The composition of claim 1 wherein the compound of Formula I is N-(aminocarbonyl)-2,3-dichlorobenzenesulfonamide.

4. The composition of claim 1 wherein the compound of Formula I is N-(aminocarbonyl)-2-chlorobenzenesulfonamide.

5. The composition of claim 1 wherein the compound of Formula I is N-(aminocarbonyl)-2,3-dichlorobenzenesulfonamide.

6. The composition of claim 1 wherein the compound of Formula I is N-(aminocarbonyl)-2-chlorobenzenesulfonamide.

7. A method of protecting a graminaceous agricultural crop from injury by the use of an antidotally-effective amount of a compound of Formula I

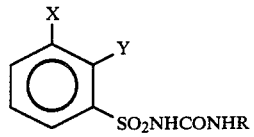
                    I wherein
X is H, F, Cl or Br;
Y is Cl or SO$_2$NR$^1$R$^2$;

R is H, C$_1$–C$_6$ alkyl, C$_5$–C$_6$ cycloalkyl, or C$_2$–C$_4$ alkyl substituted with C$_1$–C$_2$ alkoxy or C$_1$–C$_2$ alkylthio;

R$^1$ and R$^2$ are independently C$_1$–C$_2$ alkyl; provided that when Y is SO$_2$NR$^1$R$^2$, R is other than H or CH$_3$ or its agriculturally suitable salt in conjunction with the postemergence application to the locus of the crop plant of an antidotable sulfonylurea herbicide of the formula

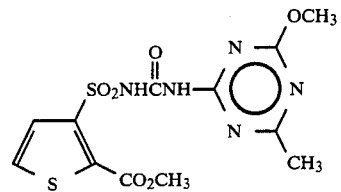
                    VIII

8. The method of claim 7 wherein the compound of Formula I is applied to the crop seed followed by the postemergence application to the locus of the crop plant of the herbicide.

9. The method of claim 8 wherein the compound of Formula I is N-(aminocarbonyl)-2-chlorobenzenesulfonamide.

10. The method of claim 7 wherein the compound of Formula I is N-(aminocarbonyl)-2-chlorobenzene sulfonamide.

* * * * *

UNITED STATES PATENT AND TRADEMARK OFFICE
CERTIFICATE OF CORRECTION

PATENT NO. : 4,645,527
DATED : February 24, 1987
INVENTOR(S) : Kofi S. Amuti and Philip B. Sweetser It is certified that error appears in the above-identified patent and that said Letters Patent is hereby corrected as shown below:

Column 1, line 31, the word "products" should be deleted and the word -- protects -- substituted therefore.

Column 20, line 66, each of the data given for the rate of 64 g/ha should be moved over one column and the data for corn to be added is "0".

Signed and Sealed this

Nineteenth Day of January, 1988

Attest:

DONALD J. QUIGG

*Attesting Officer*       *Commissioner of Patents and Trademarks*